US008990964B2

United States Patent
Anderson et al.

(10) Patent No.: US 8,990,964 B2
(45) Date of Patent: Mar. 31, 2015

(54) WELDING HELMET

(71) Applicants: David R. Anderson, Appleton, WI (US); Peter M. Gallagher, Fishers, IN (US)

(72) Inventors: David R. Anderson, Appleton, WI (US); Peter M. Gallagher, Fishers, IN (US)

(*) Notice: Subject to any disclaimer, the term of this patent is extended or adjusted under 35 U.S.C. 154(b) by 43 days.

(21) Appl. No.: 13/910,296

(22) Filed: Jun. 5, 2013

(65) Prior Publication Data

US 2014/0020147 A1 Jan. 23, 2014

Related U.S. Application Data

(60) Provisional application No. 61/674,305, filed on Jul. 21, 2012.

(51) Int. Cl.
*A61F 9/06* (2006.01)
*G02F 1/13* (2006.01)
*B23K 9/32* (2006.01)

(52) U.S. Cl.
CPC ...... *A61F 9/06* (2013.01); *G02F 1/13* (2013.01); *B23K 9/322* (2013.01)
USPC .................................................. 2/8.8; 2/8.2

(58) Field of Classification Search
CPC ........... A61F 9/06; A61F 9/061; A61F 9/062; A61F 9/064; A61F 9/065; A61F 9/068; A61F 9/067
USPC .............. 2/8.2, 8.3, 8.4, 8.5, 8.6, 8.7, 8.8
See application file for complete search history.

(56) References Cited

U.S. PATENT DOCUMENTS

| | | | | |
|---|---|---|---|---|
| 1,504,029 A | * | 8/1924 | De Rosier | 2/8.2 |
| 1,928,238 A | | 9/1933 | Willson et al. | |
| 1,994,103 A | * | 3/1935 | Huey | 2/8.2 |
| 2,187,932 A | * | 1/1940 | Cornell | 2/8.2 |
| 2,212,014 A | * | 8/1940 | Doyle | 2/8.1 |
| 2,249,239 A | * | 7/1941 | Goldsmith | 2/8.5 |
| 2,397,009 A | | 3/1946 | Hurley et al. | |
| 2,628,530 A | * | 2/1953 | Rabben | 351/44 |
| 2,907,041 A | | 10/1959 | Finn | |
| 4,649,571 A | * | 3/1987 | Falkiner | 2/8.5 |
| D324,588 S | | 3/1992 | Metzger | |
| D342,347 S | | 12/1993 | Chen | |
| 5,959,705 A | * | 9/1999 | Fergason | 349/14 |
| 6,067,129 A | * | 5/2000 | Fergason | 349/14 |
| 6,341,863 B1 | | 1/2002 | Chen-Lieh | |
| 6,483,090 B1 | * | 11/2002 | Bae | 250/201.1 |
| 6,552,316 B1 | * | 4/2003 | Bae | 250/201.1 |
| 6,614,409 B1 | | 9/2003 | Bae | |
| 7,008,055 B2 | * | 3/2006 | McLear et al. | 351/44 |
| 7,305,719 B2 | | 12/2007 | Pan | |
| 7,342,210 B2 | * | 3/2008 | Fergason | 250/206 |
| 7,470,880 B2 | * | 12/2008 | Huh | 250/205 |
| 7,564,014 B2 | * | 7/2009 | Huh | 250/205 |
| 8,081,262 B1 | * | 12/2011 | Perez | 349/14 |

(Continued)

OTHER PUBLICATIONS

PCT International Search Report for PCT/US2013/051037 filed Jul. 18, 2013.

*Primary Examiner* — Danny Worrell
(74) *Attorney, Agent, or Firm* — Rathe Lindenbaum LLP

(57) ABSTRACT

A welding helmet comprises a face cover, a first pane and a second pane. The face cover comprises a panel extending across an entire face of a person. The first pane comprises auto darkening material supported by the face cover panel so as to extend in a first flat plane. A second pane comprises auto darkening material supported by the face cover panel so as to extend in a second flat plane oblique to the first flat plane.

20 Claims, 5 Drawing Sheets

(56) References Cited

U.S. PATENT DOCUMENTS

2005/0007504 A1* 1/2005 Fergason ................. 349/14
2006/0010551 A1 1/2006 Bishop et al.
2007/0056072 A1* 3/2007 Steinemann ................ 2/8.8
2009/0094721 A1* 4/2009 Becker ................. 2/8.8
2010/0090997 A1 4/2010 Huh
2011/0248864 A1 10/2011 Becker et al.
2012/0081162 A1 4/2012 Greiner et al.

* cited by examiner

WELDING HELMET

CROSS-REFERENCE TO RELATED PATENT APPLICATIONS

The present application claims priority under 35 USC 119 from U.S. provisional patent application Ser. No. 61/674,305 filed on Jul. 21, 2012 by David R. Anderson and Peter M. Gallagher and entitled WELDING HELMET, the full disclosure of which is hereby incorporated by reference.

BACKGROUND

Welding helmets are worn by welders to shield a welders face from heat and sparks as well as to filter out optically harmful ultraviolet and infrared rays or electromagnetic radiation. Existing welding helmets may provide inadequate vision to a welder.

DETAILED DESCRIPTION OF THE EXAMPLE EMBODIMENTS

This disclosure relates to a welding helmet that comprises a plurality of separate panes or lenses of auto darkening material, wherein the panes are formed from a material that has a darkness or shading that is adjustable (automatically in response to sensed light or under manual control). In one implementation, the material automatically adjusts its darkness or shading to sensed light. Compared to passive welding lenses that are made in a single shade that never changes, auto darkening materials automatically change in milliseconds to go from a lighter shade the operator can see through to a darker shade that protects the welder from the intensely bright welding arc and harmful UV and IR rays.

While looking through the lens in the light state the operator is able to view the working area allowing them to position the material and get the welding gun/torch in position to weld. When the welding arc begins the lens switches from a lighter (3.5-4) shade to a darker (shade 5-13) shade selected by the operator to meet their protection needs. This helps keep the welder in place and not loose welding position while starting the arc as is a common complaint with older passive technology. With such passive technology the operator would have to set the materials and gun/torch and then without hands position the helmet in place with a nod of the head and significant chance they will get out of position in the process.

This lens technology uses LCD (liquid crystal display) which can be changed into a variety of shades (generally shade 3.5-13) by use of electronic controls and power. The lower shades can be seen through easily allowing the operator to view the working area and also perform a grinding function. Shade 5 is recommended for gas welding and other higher shades are used for plasma cutting and various forms of welding. The short coming of this technology is that the width of a single lens is limited and reduces the peripheral viewing area. The use of multiple Auto-Darkening lenses set at an angle greatly increases the peripheral viewing ability of the operator without increasing the width of the helmet.

Figure 1:
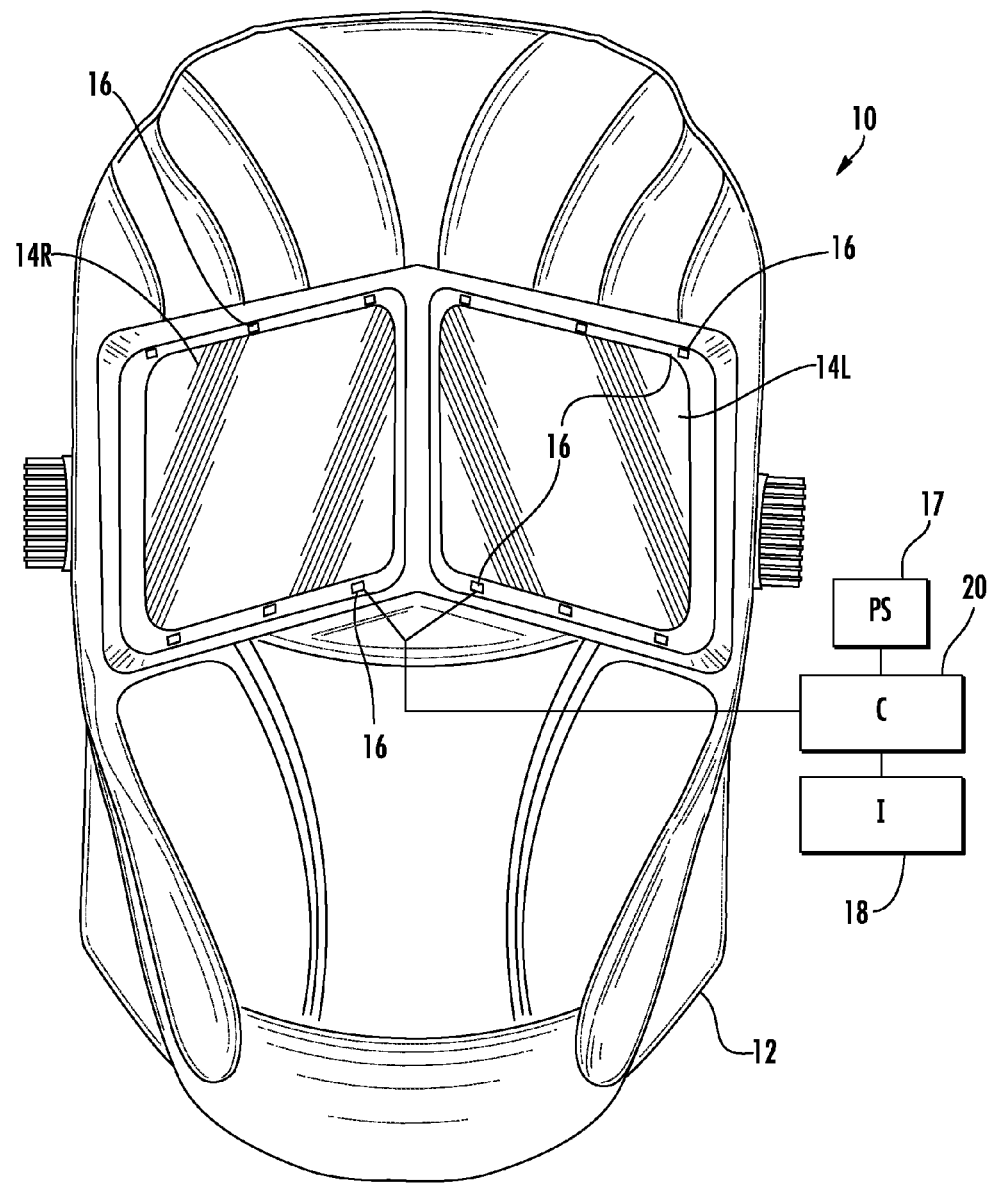
FIG. 1 is a front perspective view of an example welding helmet.
Figure 2:
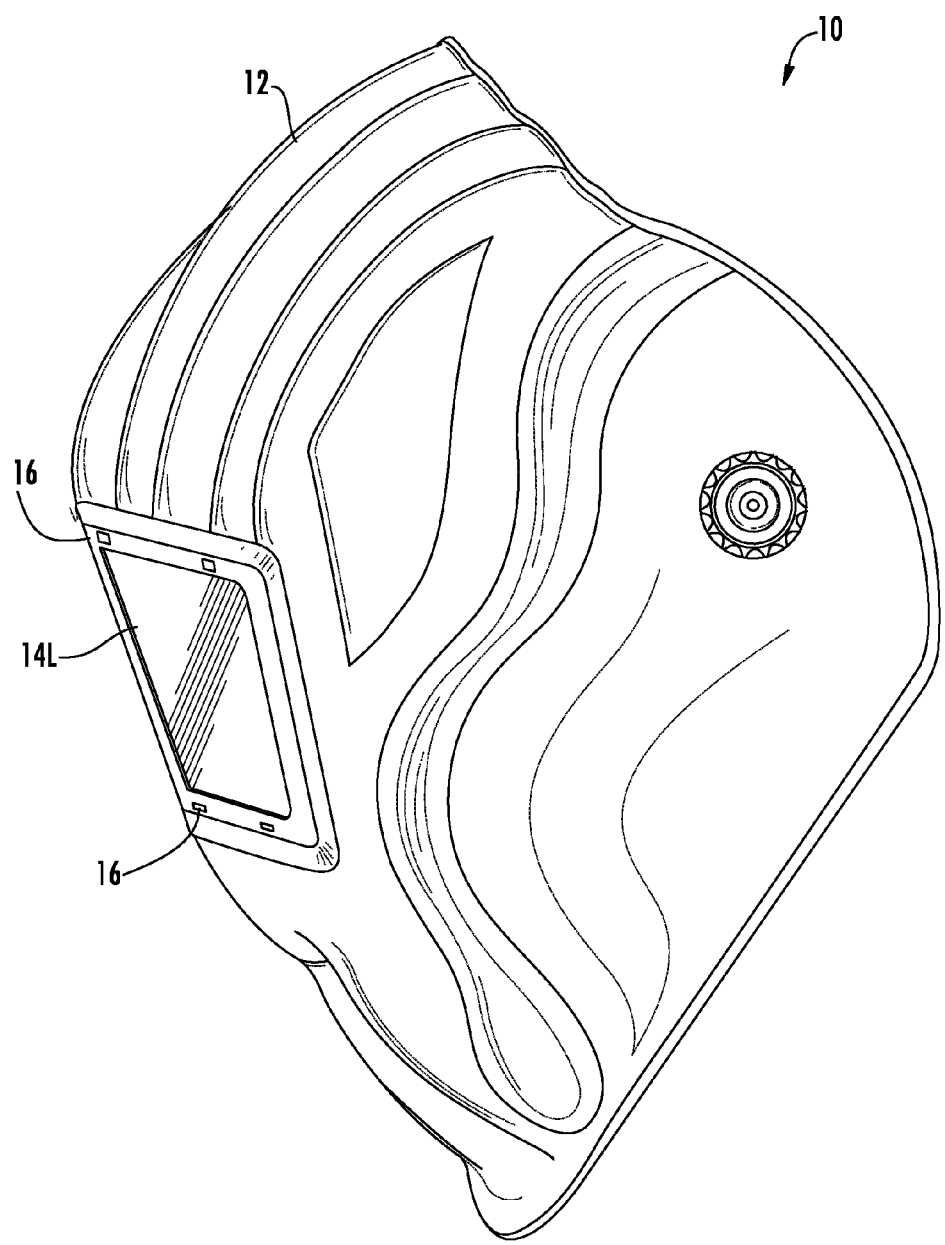
FIG. 2 is a side elevational view of the welding helmet of FIG. 1.

FIGS. 1 and 2 illustrate an example welding helmet 10. Welding helmet 10 comprises face cover panel 12, left and right panes 14L, 14R, respectively, (collectively referred to as panes 14), light sensors 16, power source 17, input 18 and controller 20. Face cover panel 12 comprises a mask, face guard or panel that extends across substantially the entire face of a person wearing helmet 10 so as to cover the person eyes, nose, mouth, ears, neck, forehead, top of head, and chin.

Panes 14 comprise flat panels, lenses or shutters of adjustable shading material, such as a liquid crystal shutter. Panes 14 adjust a shading or a darkness level in response to control signals generated based upon either a sense light through sensor 16 and/or based upon signals based upon a selection through input 18. Each of panes 14 is formed as a parallelogram, nominally a rhombus, to optimize viewing range. In other implementation panes 14 may have other shapes. Panes 14 are constructed so as to satisfy standards of ANSI regarding welding helmets.

As shown by FIG. 2, panes 14 extend in flat planes that are oblique to one another, with each pane 14 angled towards opposite sides of the forward direction in which panel 12 faces. In one implementation, panes 14 are angled between 100 and 175 degrees with respect to a vertical plane extending perpendicular to the forward direction in which panel 12 faces. In other implementations, panes 14 may be provided at other angles. Although panes 14 are illustrated as having rectangular shapes, in other implementations, panes 14 may have other shapes.

Light sensors 16 comprises one or more light sensing devices configured to sense or detect changes in light in front of panes 14 and to generate signals which are transmitted to controller 20. In the example illustrated, light sensors 16 is arranged around each of panels 14. Although for ease of illustration, only a few of sensors 16 are illustrated as being connected to controller 20, controller 20 is in communication with each of the sensors 16 shown. In other implementations, light sensors 16 may additionally or alternatively detect changes in electromagnetic fields which may be experienced during welding.

Figure 3:
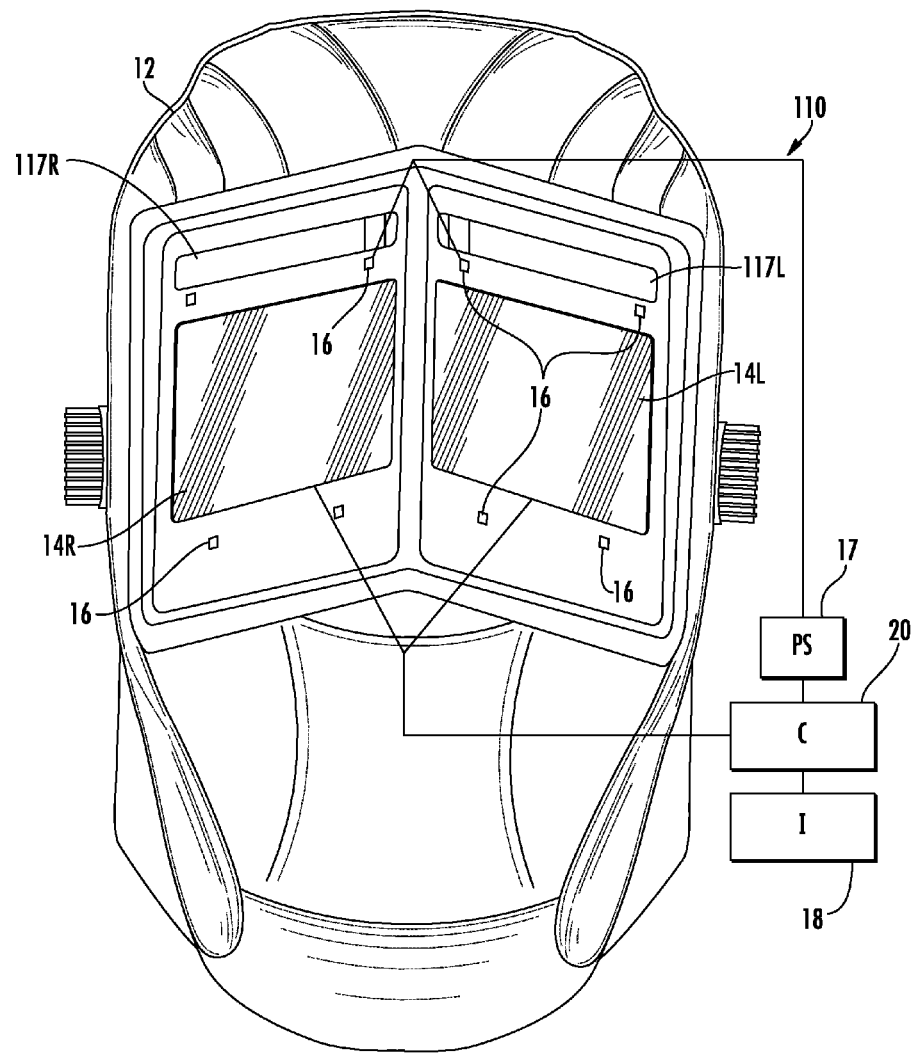
FIG. 3 is a front perspective view of another implementation of the welding helmet of FIG. 1.
Figure 4:
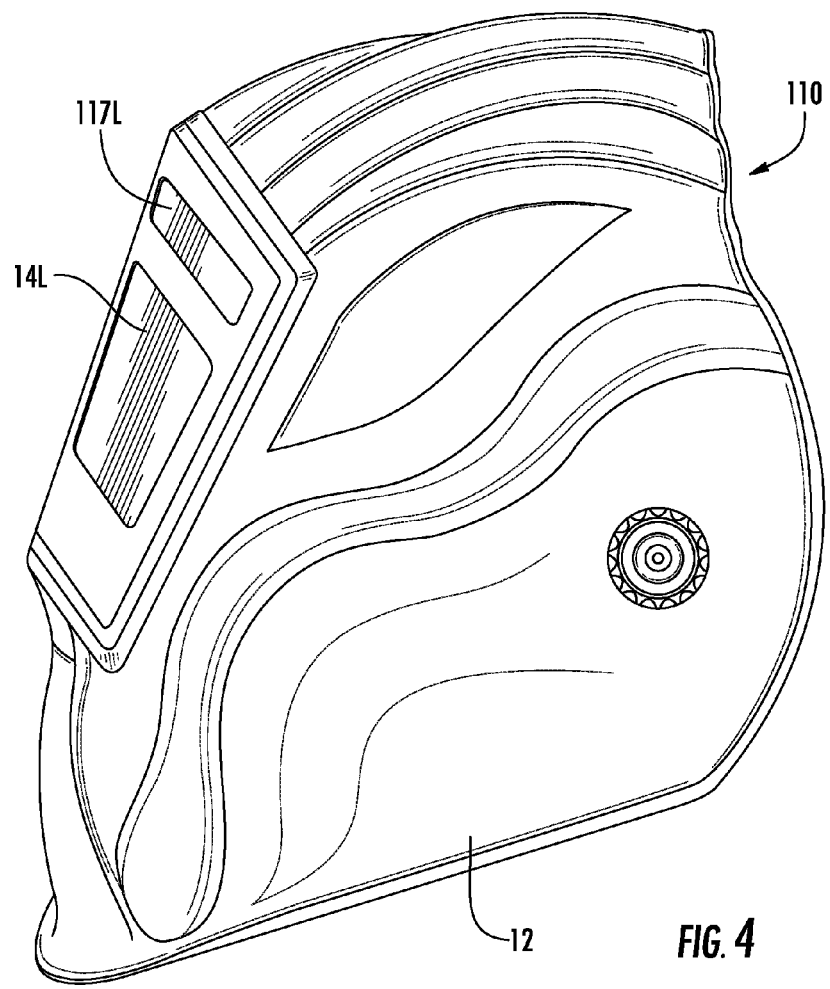
FIG. 4 is a side elevational view of the welding helmet of FIG. 3.

Power source 17 supplies power to each of controller 20, input 18, sensors 16 and panes 14. In the example illustrated, power source 17 comprises a battery, rechargeable in one implementation or disposable in another implementation. In other implementations, such as shown in FIGS. 3 and 4, power source 17 may be provided by solar bars located above panels 14 which power the unit and charge a rechargeable battery.

Input 18 comprises one or more devices to receive selections or commands from a person for selecting parameters for the control or operation of panes 14. In one implementation input 18 may comprise one or more dials, buttons, switches and the like directly carried by helmet 10 to control or adjust shade darkness level, sensitivity level, delay timing or to fix the shade in a grinding mode shade. In another implementation, input 18 may comprise a touch screen, touchpad, a keyboard, keypad of the like which is in a wired or wireless communication with a receiver or transmitter carried by helmet 10. In one implementation, input 18 facilitates input of commands or selections switching, 10 between different modes. In one implementation, input 18 facilitates input of selections selecting or defining upper or lower limits for shading ranges. In those implementations where panes 14 automatically adjust in response to sense light between predefined shades or darkness levels, (manually adjustable) input 18 may be omitted. (shade, sensitivity and delay can be internally set or fixed and built into controller C).

Controller 20 comprises one or more processing units configured to receive signals from light sensor 16 and input 18 (in those implementation that have input 18), wherein controller 20 generates control signals to control a shading or darkness level of panes 14. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 20 may be embodied as part of one or more application-specific integrated circuits (ASICs). Unless otherwise specifically noted, the controller is not limited to any specific combination of hardware circuitry and software, nor to any particular source for the instructions executed by the processing unit.

In one implementation, controller 20 utilizes selected upper and/or lower darkness settings received through input 18 to automatically adjust the shading or darkness level of panes 14 in response to detected changes in light as detected by light sensor 16. For example, a person may enter a selection through input 18 indicating that the upper adjustable setting for the darkness should be 10, wherein upon detecting a change in light and/or electromagnetic field necessitating an increase in shading, controller 20 generates control signals causing pane 114 to automatically increase the shading or darkness level of panes 14 to the input upper setting of 10. In another implementation, controller 20 may actuate panes 14 between different modes. For example, in a first mode, panes 14 may automatically change between different darkness levels in response to sensed light and/or electromagnetic field. In a second mode, panes 14 may be fixed at a selected darkness level or shading level, independent of light and/or electromagnetic field being sensed by sensor 16. In another mode, controller 20 may independently control each of panes 14 to different adjustable upper darkness settings and adjustable lower darkness settings based on sensed light and/or electromagnetic field. In one implementation, the user may further input settings to adjust the thresholds at which panes change to different darkness settings. In such implementations, a person may select a threshold of X and a setting of Y, wherein upon sensing a light and/or electromagnetic field satisfying the threshold X, controller 20 adjusts the darkness level of panes 14 to the darkness setting of Y.

FIGS. 3 and 4 illustrate welding helmet 110, another implementation of welding helmet 10. Welding helmet 110 is similar to welding helmet 10 except that, helmet 110 includes power sources 116, 117 in addition to power source 17. Power sources 117R and 117L comprise solar panels for powering welding helmet 110 and/or charging a battery serving as power source 17 of welding helmet 110.

Figure 5:
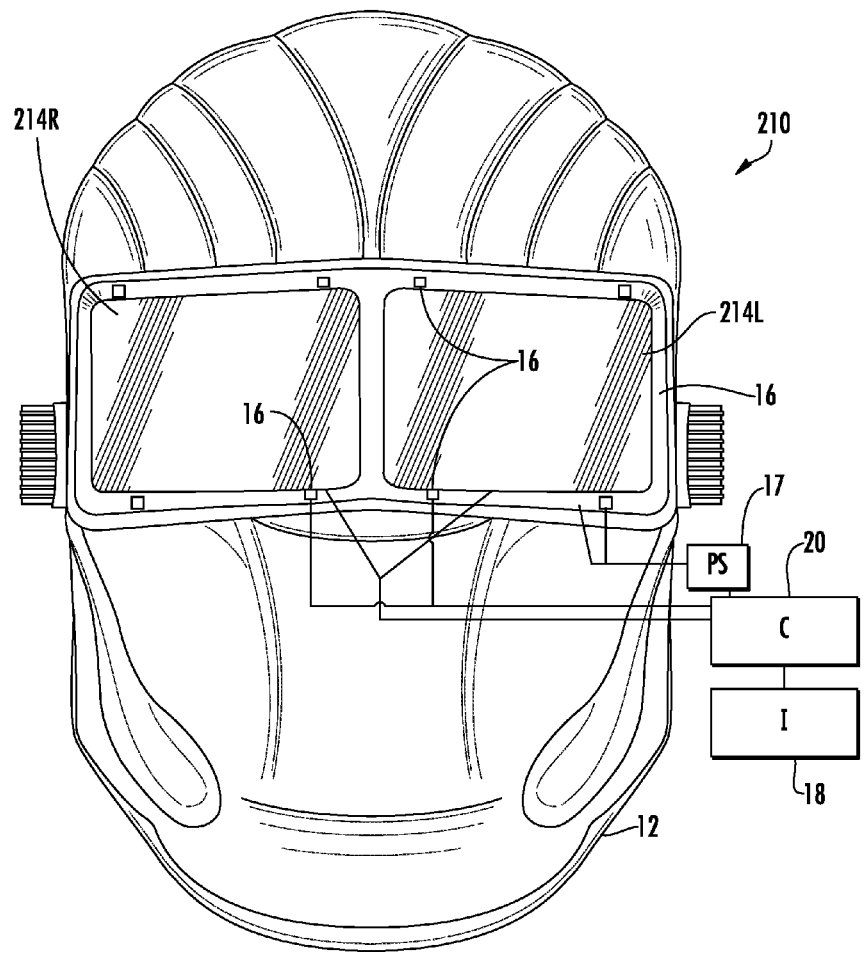
FIG. 5 is a front elevational view of another implementation of the welding helmet of FIG. 1.

FIG. 5 illustrates welding helmet 210, another implementation of welding helmet 10. Welding, 210 is similar to welding helmet 10 except that welding, 210 includes frames 214R and 214L. Frames 214 are identical the frame 14 except that frame 14 is rectangular in shape. Like frame 14, frames 214 extend in flat planes which are oblique to one another and which face forward outwardly away from a centerline of panel 12 in direction towards opposite sides of helmet 210.

Although the present disclosure has been described with reference to example embodiments, workers skilled in the art will recognize that changes may be made in form and detail without departing from the spirit and scope of the defined subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A welding helmet comprising:
   a face cover panel to extend across an entire face of a person;
   a first pane of auto darkening material supported by the face cover panel and extending in a first flat plane; and
   a second pane of auto darkening material supported by the face cover panel and extending in a second flat plane oblique to the first flat plane, wherein the face cover panel faces in a first forward direction, wherein the first pane faces in a first side direction angled with respect to the first forward direction and wherein the second pane faces in a second side direction angled with respect to the first forward direction.

2. The welding helmet of claim 1, wherein auto darkening material of the first pane and the second pane comprise auto darkening liquid crystal materials.

3. The welding helmet of claim 1, wherein the first pane is supported by the face cover panel so as to extend opposite a left eye of a person wearing the helmet and wherein the second pane supported by the face cover panel so as to extend opposite a right eye of a person wearing the helmet.

4. The welding helmet of claim 1, further comprising:
   a sensor;
   an input; and
   a controller to generate control signals based upon selections received through the input and light signals from the sensor, wherein the control signals control a shading of at least one of the first pane and the second pane.

5. The welding helmet of claim 1, wherein the first pane and the second pane automatically adjust based on signals from the sensor and wherein the control signals establish an upper limit for darkness shading.

6. The welding helmet of claim 5, wherein the control signals control a lower limit for darkness shading.

7. The welding helmet of claim 4, wherein the helmet operates in a first mode wherein the first pane and the second pane automatically adjust in response to signals from the sensor and a second mode wherein the control signals fix the first pane and the second pane at a selected darkness shading level.

8. The welding helmet of claim 4, wherein the first pane and the second pane automatically adjust based on signals from the center and wherein the control signals control a lower setting for darkness shading.

9. The welding helmet of claim 4, wherein the sensor is disposed about the first pane so as to extend both above and below the pane.

10. The welding helmet of claim 4, wherein the sensor disposed above the first pane.

11. The welding helmet of claim 4, wherein the sensor detects changes in light.

12. The welding helmet of claim 4, wherein the sensor detects changes in electromagnetic fields.

13. The welding helmet of claim 1, wherein the first pane has a parallelogram shape.

14. The welding helmet of claim 1, wherein the first pane has a rhombus shape having a perimeter side edges that extend oblique to one another.

15. The welding helmet of claim 1, wherein the auto darkening material has an upper limit setting of at least 4 (Per ANSI standards).

16. The welding helmet of claim 1, wherein the auto darkening material has an upper setting of at least 10 (Per ANSI standards).

17. The welding helmet of claim 1, wherein a top edge of each of the first pane and the second pane slope upwardly towards a centerline of the helmet extending between the first pane and the second pane.

18. The welding helmet of claim 1, wherein a bottom edge of each of the first pane and the second pane slope upwardly towards the centerline of the helmet extending between the first pane and the second pane.

19. The welding helmet of claim 1, wherein the first side direction and the second side direction diverge from one another in the first forward looking direction.

20. A welding helmet comprising:

a face cover panel to extend across an entire face of a person;

a first pane of auto darkening material supported by the face cover panel and extending in a first flat plane; and a second pane of auto darkening material supported by the face cover panel and extending in a second flat plane oblique to the first flat plane, wherein the first pane has a rhombus shape having a perimeter side edges that extend oblique to one another.

* * * * *